United States Patent [19]

Aasen et al.

[11] Patent Number: 5,525,648

[45] Date of Patent: Jun. 11, 1996

[54] METHOD FOR ADHERING TO HARD TISSUE

[75] Inventors: Steven M. Aasen, Lakeland; F. Andrew Ubel, III, St. Paul; Joel D. Oxman, St. Louis Park; Sumita B. Mitra, West St. Paul; Jon W. Fundingsland, Maplewood, all of Minn.

[73] Assignee: Minnesota Mining and Manufacturing Company, St. Paul, Minn.

[21] Appl. No.: 368,048

[22] Filed: Jan. 3, 1995

Related U.S. Application Data

[63] Continuation of Ser. No. 999,290, Dec. 30, 1992, abandoned, which is a continuation-in-part of Ser. No. 815,404, Dec. 31, 1991, abandoned.

[51] Int. Cl.$^6$ ........................................ A61K 6/08
[52] U.S. Cl. ........................... 523/116; 523/118; 523/115
[58] Field of Search ................................. 523/115, 116, 523/118

[56] References Cited

U.S. PATENT DOCUMENTS

| | | | |
|---|---|---|---|
| 3,200,142 | 8/1965 | Bowen | 260/486 |
| 3,872,047 | 3/1975 | Jandourek | 260/33.4 R |
| 3,882,600 | 5/1975 | Plymale | 32/15 |
| 3,954,475 | 5/1976 | Bonham et al. | 96/67 |
| 3,997,504 | 12/1976 | Plymale | 260/42.27 |
| 4,182,035 | 1/1980 | Yamauchi et al. | 433/228 |
| 4,212,970 | 7/1980 | Iwasaki | 542/455 |
| 4,222,780 | 9/1980 | Shibatani et al. | 106/35 |
| 4,235,633 | 11/1980 | Tomioka et al. | 106/35 |
| 4,259,075 | 3/1981 | Yamauchi et al. | 433/217 |
| 4,259,117 | 3/1981 | Yamauchi et al. | 106/35 |
| 4,368,043 | 1/1983 | Yamauchi et al. | 433/217 |
| 4,382,782 | 5/1983 | Smith et al. | 433/217 |
| 4,383,052 | 5/1983 | Higo et al. | 523/118 |
| 4,404,150 | 9/1983 | Tsunekawa et al. | 260/927 |
| 4,443,197 | 4/1984 | Fasayama et al. | 433/217 |
| 4,499,251 | 2/1985 | Omura et al. | 526/278 |
| 4,514,342 | 4/1985 | Billington et al. | 260/952 |
| 4,515,930 | 5/1985 | Omura et al. | 526/276 |
| 4,518,430 | 5/1985 | Brown et al. | 106/35 |
| 4,521,550 | 6/1985 | Bowen | 523/116 |
| 4,525,511 | 6/1985 | Kirby et al. | 524/158 |
| 4,535,102 | 8/1985 | Kusumoto et al. | 523/116 |
| 4,537,940 | 8/1985 | Omura et al. | 526/278 |
| 4,538,990 | 9/1985 | Pashley | 433/217 |
| 4,539,382 | 9/1985 | Omura et al. | 526/276 |
| 4,544,467 | 10/1985 | Bunker et al. | 204/159.24 |
| 4,553,941 | 11/1985 | Aasen | 433/228.1 |
| 4,588,756 | 5/1986 | Bowen | 523/116 |
| 4,591,649 | 5/1986 | Hirasawa et al. | 549/232 |
| 4,593,054 | 6/1986 | Asmussen et al. | 523/118 |
| 4,645,456 | 8/1986 | James | 433/217.1 |
| 4,648,845 | 3/1987 | Orlowski et al. | 527/116 |
| 4,719,149 | 1/1988 | Aasen et al. | 428/473 |
| 4,732,943 | 3/1988 | Beech et al. | 525/303 |
| 4,806,381 | 2/1989 | Englebrecht et al. | 427/2 |
| 4,964,911 | 10/1990 | Ibsen et al. | 523/116 |
| 5,130,347 | 7/1992 | Mitra | 522/149 |
| 5,334,625 | 8/1994 | Ibsek et al. | 523/115 |

FOREIGN PATENT DOCUMENTS

| | | |
|---|---|---|
| 0058483 | 8/1982 | European Pat. Off. . |
| 0155812 | 9/1985 | European Pat. Off. . |
| 029133 | 11/1988 | European Pat. Off. . |
| 0305083 | 1/1989 | European Pat. Off. . |
| 0323120 | 7/1989 | European Pat. Off. . |
| 2711234 | 9/1977 | Germany . |
| 49-31754 | 3/1974 | Japan . |
| 57-143372 | 9/1982 | Japan . |
| 57-167364 | 10/1982 | Japan . |
| 1088726 | 2/1983 | U.S.S.R. ........................ 523/115 |
| 2190383 | 11/1987 | United Kingdom ............. 520/115 |
| 2217989 | 8/1989 | United Kingdom . |

OTHER PUBLICATIONS

Munksgaard et al., Effect of five adhesives on adaptation of resin in dentin cavities. Scand J. Dent Res. 1984; pp. 544–548.

Nakabayashi et al., Studies on Dental Self–Curing Resins (21), Reports of the Institute for Medical & Dental Engineering 15. 1981; pp. 2–14.

Nakabayashi et al., The promotion of adhesion by the infiltration of monomers into tooth substrates. J. Biomed. Mater. Res., 1982; vol. 16 pp. 265–273.

Nakabayashi et al., Effect of HEMA on bonding to dentin. Dent. Mater. 1992; pp. 125–130.

Hasegawa et al., A laboratory study of the Amalgambond Adhesive System. Am. J. Dent, 1992, vol. 5, No. 4 pp. 181–186.

Mooney et al., Microleakage: effect of citric acid with ferric chloride on dentin, Abstract 56, Program of IADR Oct. 1984.

Ibsen et al., Adhesive Restorative Denistry, Saunders Company Philadelphia, 1974; pp. 39–49, 5,10–13.

Buonocore et al., A report on a resin composition capable of bonding to human dentin surface. J. Dent. Res. 1956 pp. 846–851.

(List continued on next page.)

*Primary Examiner*—Peter F. Kulkosky
*Attorney, Agent, or Firm*—Gary L. Griswold; Walter N. Kirn; Dale A. Bjorkman

[57] ABSTRACT

The invention provides a pretreatment method and primer that is applied directly to the hard tissue. The invention has particular utility for adhering to or coating sclerotic dentin and cervical enamel or for adhering to or coating hard tissue in a high humidity environment. The primer enables formation of extremely strong bonds to dentin. The method comprises the steps of:

(a) applying to the hard tissue adhesively effective amounts of an acid and a water-dispersible film former comprising a polymer and (b) hardening the film former.

Primer compositions are provided for use in this method, comprising a mixture of an acid and a film former comprising a polymer prior to hardening, the mixture being in the form of a film atop the hard tissue.

20 Claims, No Drawings

OTHER PUBLICATIONS

Munksgaard et al., Bond Strength between Dentin and Restorative Resins mediated by mixtures of HEMA and Glutaldehyde, J. Dent. Res. Aug. 1984, vol. 63, pp. 1087–1089.

Munksgaard, e. c. et al., Dentin–Polymer Bond Promoted by Gluma and Various Resins, J. Dent. Res., Dec. 1985, pp. 1409–1411.

M. Buonocore, "The Challenge of Bonding to Dentin", *The Acid Etch Technique,* (St. Paul, 1974).

Product Instructions for Dentin/Enamel Bond from Coltene Company.

E. Asmussen and E. C. Munksgaard, "Adhesion of Restorative Resins to Dentinal Tissues"; D. R. Beech, Bonding of Restorative Resins to Dentin; and Open Discussion of Asmussen/Beech Papers, *Posterior Composite Resin Dental Restorative Materials,* pp. 217–241 (1985).

M. Jensen, *International Symposium on Posterior Composite Resin Dental Restorative Materials,* 243–44 (1985).

L. Tao and D. H. Pashley, *Dental Materials,* vol. 5, 133–39 (1989).

D. H. Pashley, *Scanning Microscopy,* vol. 3, No. 1, 161–76 (1989).

Prosser et al., *Developments in Ionic Polymers–1,* Chapter 5, Applied Science Publishers (London and New York, 1983).

E. C. Munksgaard, M. Irie, and E. Asmussen, *J. Dent. Res.,* 64 (12:1409–1411), (1985).

M. Buonocore, *J. Dent. Res.* 34, 849, (1955).

"Lee Clense & Bond I Application Procedure with Elapsed Times:" (Brochure of Lee Pharmaceuticals, undated).

Product Literature: Syntac™ Enamel/Dentin Bonding System. (Brochure of Vivadent USA).

Ruyter et al. NIOM pp. 133–146 Acta Odontol. Scand. 1981.

METHOD FOR ADHERING TO HARD TISSUE

RELATED APPLICATIONS

This is a continuation of application Ser. No. 07/999,290 filed Dec. 30, 1992, now abandoned, which is a continuation-in-part of application Serial No. 07/815,404, filed Dec. 31, 1991, now abandoned.

TECHNICAL FIELD

This invention relates to a method for adhering to hard tissue. This invention also relates to adhesive compositions for use on hard tissue.

BACKGROUND ART

In recent years there has been intense interest in the dental field in adhesives that bond to hard tissues such as dentin. Forces generated by the polymerization contraction of dental restorative materials suggest that a minimum adhesion strength for bonding restorative materials to hard surfaces in in vivo clinical procedures would be desirable. For example, M. Jensen, Polymerization Shrinkage and Microleakage *International Symposium on Posterior Composite Resin Dental Restorative Materials*, 234–44 (1985) reports a contraction force of 7.3 MPa. for conventional composite materials. In many instances the minimum adhesive strength has not been achieved, resulting in direct communication between dentin and the oral cavity via gaps between the dental restorative material and the cavity walls. This may be responsible, in part, for patient complaints of sensitivity and for pulpal irritation and inflammation. See, Tao, The relationship between dentin bond strengths and dentin permeability *Dental Materials*, Vol. 5, 133–39 (1989).

Recently a novel priming method was developed in the laboratory of the assignee of this invention and is sold commercially as ScotchBond 2™ Light Cure Dental Adhesive with Scotchprep™ Dentin Primer (commercially available from 3M). This priming method has achieved average shear strengths in vitro in excess of 20 MPa. U.S. Pat. No. 4,719,149 (Aasen et at.) describes that invention as an acid and a water-soluble film former useful for priming hard tissue (e.g., dentin). The acid has a pKa less than or equal to that of phenol. The calcium salt(s) of the acid are soluble in the film former. The film former is exemplified as comprising various difunctional and monofunctional monomers and optional cosolvents with 2-hydroxyethylmethacrylate and water being preferred.

Kusumoto et at., U.S. Pat. No. 4,535,102 discloses an adhesive coating material for a hard tissue comprising (1) a polymer having an acid value of 30 to 700 and including in recurring units a hydrophobic group and two carboxyl groups or one carboxylic anhydride group bonded to the polymer, and (2) a polymerizable vinyl compound or a mixture of said polymerizable vinyl compound and an organic titanate compound.

Engelbrecht et al., U.S. Pat. No. 4,806,381 discloses oligomeric or prepolymeric organic compounds that contain both polymerizable unsaturated groups and acid radicals, their salts or their reactive-derivative radicals. The compounds adhere to biological substrates such as tooth tissue.

Beech et al., U.S. Pat. No. 4,732,943 discloses an adhesive comprising (a) a condensate of ε-caprolactone with one or more acrylic monomers containing hydroxy groups and (b) a polymer containing binding groups capable of binding to the dentin.

One major limitation in the prior art has been the difficulty of adhering to hard tissue which is not dry. This necessitates maintaining a dry tooth surface during the priming procedure which is in practice difficult to ensure. For instance, the oral cavity is inherently humid and the hard tissue is susceptible to fluid perfusion from the pulp chamber. The susceptibility of the tooth surface to this fluid perfusion is believed to be a function of the proximity of the prepared surface to the pulp chamber. Near the pulp, the tubules are very close together and the water content of this deep dentin is very high. See, Pashley, Dentin: A Dynamic Substrate *Scanning Microscopy*, Vol. 3, No. 1, 161–76 (1989).

Additionally, dental materials adhere poorly to sclerotic dentin and cervical enamel. Sclerotic dentin is characterized as hypermineralized dentin (i.e., the dentinal tubular contents are mineralized) and has a coloration that can range from transparent to intense yellow or yellow-brown.

SUMMARY OF THE INVENTION

The invention provides a pretreatment (a primer) that is applied directly to the hard tissue. The invention has particular utility for adhering to or coating sclerotic dentin and cervical enamel or for adhering to or coating hard tissue in a high humidity environment. The primer enables formation of extremely strong bonds to dentin (including sclerotic dentin), exhibiting shear strengths as high as 30 MPa., when tested in shear using the procedure described herein. Tests to date indicate that an extremely durable adhesive bond with little or no detectable microleakage can be obtained. The primers of the invention can, if desired, be water-based, thus substantially reducing the need to apply them in a dry field. The primers of the invention work very well in high humidity environments or when bonding to sclerotic dentin.

The present invention provides, in one aspect, a method for adhering to or coating hard tissue, comprising the steps of:

(a) applying to the hard tissue adhesively effective amounts of an acid and a water-dispersible film former comprising a polymer and (b) hardening said film former.

For purposes of this invention "hardening" is defined as the formation of a covalently or ionically crosslinked polymer as opposed to merely drying a previously prepared polymer of its carder solvent or merely cooling a previously melted thermoplastic polymer.

The present invention also provides novel primer compositions for use in such method, comprising a mixture of an acid and a film former comprising a polymer prior to the hardening step, said mixture being in the form of a film atop said hard tissue.

DETAILED DESCRIPTION

In the practice of the present invention, the hard tissues which can be adhered to or coated include human and animal tissues such as teeth (including the component parts which are enamel, dentin, and cementum), bone, fingernails, and hoofs. The invention has particular utility for adhering to or coating dentin, sclerotic dentin, enamel, and cervical enamel.

The acid and film former can be applied to hard tissue concurrently or sequentially. If they are applied sequentially, then if desired the acid can be rinsed from the hard tissue (e.g., using a water rinse) before application of the film former, or the film former can be applied to the acid without an intermediate rinsing step. For brevity, formulations comprising the film former will sometimes be referred to as the "primer," regardless of whether the concurrent or sequential application method is employed. Thus, when the acid and film former are applied to the hard tissue concurrently, then the acid and film former will sometimes be referred to collectively as the "primer". When the acid and film former are applied to the hard tissue sequentially, then the acid, if in a solvent, will sometimes be referred to as an "etchant" and the film former will sometimes be referred to as the "primer."

In one method of the invention, the primer is permitted to stand on the hard tissue for a desired period of time, readily volatile cosolvents are removed therefrom (e.g., by air-drying) to modify the surface of the hard tissue and leave a residual film on the surface of the hard tissue (and in the case of dentin to form a "hybrid layer" with the hard tissue), the residual film is overcoated with a layer of additional film former (the additional film former can be water-soluble or water-insoluble but should preferably form a homogeneous solution when combined with the residual film), then the additional film former and residual film are hardened and optionally overcoated with a composite, restorative, glass ionomer cement, sealant or other hardenable coating (hereafter such composites, restoratives, glass ionomer cements, sealants, and other hardenable coatings will be referred to collectively as "restoratives"). As used herein, "surface modified hard tissue" refers to hard tissue that has been exposed to the primers of the invention. As used herein, "hybrid layer" refers to the layer of resin-reinforced dentin that consists of collagen and perhaps hydroxyapatite that is infiltrated and surrounded by the monomers, oligomers and polymers of the film former and the optional additional film former. Thus the invention enables priming of hard tissue in order to improve the bond strength or durability of a restorative or coating applied thereto.

Acids for use in the present invention can be inorganic or organic acids, and if organic can be monomeric, oligomeric or polymeric. If desired, a precursor to the acid such as an acid anhydride, e.g., 4-Methacryloxyethyl Trimellitate Anhydride (4-META), acid halide (including inorganic acid halides such as Lewis acids, e.g., ferric chloride, and organic acid halides), or ester can be used in place of the acid itself, e.g., to generate the desired acid in situ. Suitable acids include mineral acids, carboxylic acids, sulfonic acids, and phenols, with carboxylic acids, alkylsulfonic acids, arylsulfonic acids, and phosphonic acids being preferred.

The acid has a pKa in water that is less than or equal to that of phenol. Preferably, the pKa of the acid is between about −20 and about +10, more preferably between about −10 and about +5.

The acid, when applied concurrently with the film former, should be sufficiently soluble in the film former and in a sufficient amount (including any optional cosolvents that are present in the film former) to provide the desired degree of adhesion for the particular hard tissue and application involved. For example, on dentin the degree of adhesion preferably is sufficient to provide an average measured shear strength of at least 7 MPa., and more preferably at least 12 MPa. Preferably, on dentin the degree of adhesion is sufficient to provide an average measured shear strength in a humid environment (i.e., as tested in a room temperature humidity chamber with a relative humidity greater than about 90% ) of at least 5 MPa., more preferably at least 7 MPa., and most preferably at least 12 MPa.

Preferably, the calcium salt of the acid is also soluble in the film former (including any optional cosolvents that are present in the film former) or in the etchant solution (e.g., when the acid is applied sequentially with the film former). Acids having insoluble calcium salts may also be used in the primers of the present invention. For example, when the acid and film former are applied sequentially the acid may form insoluble calcium salt(s) that are insoluble in: the optional cosolvent; the subsequently applied film former (including any optional cosolvents that are present in the film former); or both. However, these salt(s) can be rinsed from the hard tissue, prior to application of the film former, to thereby not detrimentally affect the adhesion.

A "soluble" acid or calcium salt of an acid, as used herein, is an acid or salt that when mixed with the film former (including any optional cosolvents that are present in the film former) under the desired conditions of use dissolves to form a homogeneous liquid mixture. Such conditions of use include temperature (e.g., body temperature), time (e.g., "standing time", that is, the amount of time the primer is allowed to remain on the surface of the hard tissue before hardening of the film former), and concentration (e.g., the concentration of acid and of calcium salt that may be formed in the film former when primer is applied to calcium-containing hard tissue such as teeth or bones). Alternatively, when the acid and film former are applied sequentially a "soluble" acid or calcium salt of an acid, as used herein, is an acid or salt that when mixed with an optional cosolvent under the desired conditions of use dissolves to form a homogeneous liquid mixture.

The acid can be liquid or a solid; if a solid it should be dissolved in a suitable solvent to enable the acid to wet the hard tissue. Liquid acids can also be dissolved in a suitable solvent, e.g., in order to facilitate wetting. Preferred solvents for the acid are the film former cosolvents discussed in more detail below.

Suitable inorganic acids include HBr, HCl, and $HNO_3$. Suitable organic acids include acetic acid, a-chloropropionic acid, 2-acrylamido-2-methylpropane sulfonic acid, acrylic acid, benzenesulfonic acid, benzoic acid, bromoacetic acid, 10-camphorquinonesulfonic acid, 10-camphorsulfonic acid, chloroacetic acid, citraconic acid, citric acid, dibromoacetic acid, dichloroacetic acid, di-Hema ester of 1,2,4,5-benzene-tetracarboxylic acid, 2,4-dinitrophenol, formic acid, fumaric acid, 2-hydroxy-4-methoxybenzophenone-5-sulfonic acid, maleic-acid, methacrylic acid, 2-naphthalene sulfonic acid, nitric acid, oxalic acid, p-nitrophenol, phenol, phosphoric acid, phosphorous acid esters (such as 2,2 '-bis(a-methacryloxy-b-hydroxypropoxyphenyl)propane diphosphonate (Bis-GMA diphosphonate), dibutyl phosphite, di-2-ethylhexyl phosphate, di-2-ethyl-hexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), pivalic acid, propionic acid, sulfuric acid, toluene sulfonic acid, tribromoacetic acid, trichloroacetic acid, trifluoroacetic acid, trifluoromethanesulfonic acid, and trihydroxybenzoic acid. Mixtures of such acids can be used if desired.

When the acid and film former are applied concurrently, then a preferred amount of acid to be dissolved in the film former will be between about 0.001M and the limit of solubility. The optimum amount depends in pan on the pKa of the acid. For example, for sulfonic acids, concentrations between about 0.01M and about 0.5M are preferred. When the acid and film former are applied sequentially, then a preferred amount of acid to be dissolved in the cosolvent will be between about 0.001M and the limit of solubility. The optimum amount depends in part on the pKa of the acid.

The film former is a water-dispersible substance or water-dispersible mixture of substances, such substance(s) being organic monomers, oligomers, polymers, or cosolvents, wherein the film former contains at least one polymer prior to the hardening step, and is capable of forming a hardenable (e.g., polymerizable) continuous or semicontinuous film on the surface of the hard tissue. As used herein, a "water-dispersible" film former has a water dispersibility or more preferably a water solubility (exclusive of any water that may be present in the film former) of at least about 5 weight percent. Most preferably, the film former can be mixed with water in all proportions. For brevity, dispersible and soluble will sometimes be referred to collectively as dispersible. As used herein, "solubility" means the capability of a substance to form a solution, i.e., either a true solution or a colloidal solution. A true solution being a uniformly dispersed mixture at the molecular or ionic level, of one or more substances (the solute) in one or more substances (the solvent). These two parts of a solution are called phases. A colloidal dispersion is often called a solution. Since colloidal particles are larger than molecules it is strictly incorrect to call such dispersions solutions; however this term is widely used in the literature. As used herein, "dispersibility" means the capability of a substance to form a dispersion, i.e., a two-phase system where one phase consists of finely divided particles (often in the colloidal size range) distributed throughout a bulk substance, the particles being the disperse or internal phase and the bulk substance the continuous or external phase.

Preferred film formers contain one or more substances having a sufficient number of water-dispersing groups such as hydroxyl groups, carboxyl groups, sulfonic acid groups, cationic salts (e.g., ammonium, phosphonium or sulfonium groups), amide linkages or polyether linkages to render the film former water-dispersible. The film former, prior to removal of any volatile components, preferably wets the hard tissue and most preferably has a sufficiently low viscosity to enable it to flow into interstices that already exist in the surface of the tissue or that are created therein by the action of the acid. After removal of any volatile components the film former preferably has a sufficiently high viscosity to enable it to resist displacement by dentinal fluids or other extraneous liquids. To assist in hardening the film former, it preferably contains one or more polymerizable substances. Addition polymerizable substances (e.g., vinyl compounds such as acrylates and methacrylates) are especially preferred. The film former can also contain appropriate polymerization catalysts (e.g., photoinitiators) to assist in hardening the film former.

Suitable polymer components in the film former include linear, branched or cyclic polymers formed prior to the hardening step. For purposes of this invention, a polymer is a chemical compound having at least two repeat units. They can be polymers of ethylenically unsaturated monomers or they can be polymeric compounds like polyester, polyamide, polyether, polyethyleneglycol, polyethyleneglycol dimethacrylate and diacrylate, polysaccharide, cellulosic, polypropylene, polyacrylonitrile, polyurethane, poly(vinyl chloride), poly(methyl methacrylate), phenol-formaldehyde, melamine-formaldehyde, and urea-formaldehyde. Mixtures of such polymers can be used if desired.

Preferred polymers are the polymers of ethylenically unsaturated monomers. These polymers may be homo- or co-polymers and may contain hydrophilic or hydrophobic groups. The polymer may optionally contain acid groups, their salts, or their reactive derivative groups. Particularly preferred polymers contain reactive groups that further react (i.e., crosslink or copolymerize) with the other components of the film former, the overcoat resin (i.e., the additional film former), or the dental restorative. Addition polymerizable reactive groups (e.g., vinyl groups such as acrylates and methacrylates) are especially preferred. Polymers of ethylenically unsaturated monomers are often used in dental glass ionomer cements. These polymers are especially useful in the present invention as they generally have good biocompatibility, are dispersible in water and have a suitable molecular weight. Particularly preferred polymers contain functional groups that have an affinity for the hard tissue. For example, such groups include β-dicarbonyl groups and carboxylic acid groups. The polymer component of an ionomer cement is often a copolymer of acrylic acid and itaconic acid, although other monomers may be incorporated, and are herein referred to as polyalkenoic acids. See generally, Prosser et al., Developments in Ionic Polymers-1, Chapter 5, Applied Science Publishers (London and New York, 1983). Recently such polymers have been further modified in the laboratory of the assignee of this invention by the incorporation of addition polymerizable reactive groups as mentioned above. Their preparation is described in European Patent Application No. 0 323 120 and in U.S. Pat. No. 5,130,347.

Suitable polymeric compounds of the invention have a weight average molecular weight prior to hardening of more than about 500, although preferably no greater than 2,000,000. More preferably, polymeric compounds of the invention have a weight average molecular weight prior to hardening of between about 1,000 and 1,000,000 evaluated against a polystyrene standard using gel permeation chromatography. Most preferably, polymeric compounds of the invention have a weight average molecular weight prior to hardening of between about 5,000 and 200,000.

Suitable monomer components in the film former include 2-hydroxyethylacrylate, 2-hydroxyethylmethacrylate ("HEMA"), 2- and 3-hydroxypropylacrylate and methacrylate, 1,37 and 2,3-dihydroxypropylacrylate and methacrylate, 2-hydroxypropyl-1,3-diacrylate and dimethacrylate, 3-hydroxypropyl-1,2-diacrylate and dimethylacrylate, pentacrythritol. diacrylate and dimethacrylate, acrylic acid, methacrylic acid, 2-trimethylammonium ethylmethacrylic chloride, 2-acrylamido-2-methylpropane-sulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, polyethyleneglycol (400) diacrylate and dimethacrylate, glycerol dimethacrylate and diacrylate, glycerol monomethacrylate and monoacrylate, pentacrylthritol trimethacrylate and triacrylate, and mixtures thereof. It is expected that where an acrylate monomer is suitable the methacrylate analog will likewise be suitable.

The film former preferably comprises one or more suitable cosolvents. The cosolvent(s) aid in wetting the hard tissue and in solubilizing or dispersing the substances. Suitable cosolvents include water, alcohols such as methanol, ethanol, 1-propanol, 2-propanol, and 2-methyl-2-propanol, ketones such as acetone and methylethylketone, aldehydes such as formaldehyde, acetaldehyde, propionaldehyde, acrolein, glutaraldehyde and 2-hydroxyadipaldhyde, amides such as acetamide and N,N-dimethylformamide, and other substances such as tetrahydrofuran and dimethyl sulfoxide. The film former preferably contains less than about 95 weight percent cosolvent, more preferably between about 15 and about 85 weight percent cosolvent.

The primer may contain only acid and film former. Other adjuvants such as polymerization catalysts, medicaments, fluoride compounds, indicators, dyes, wetting agents, buffering agents, thixotropes and the like can be included in the primer, contingent upon attainment of the desired degree of bonding performance and suitability for use on the desired hard tissue.

Hard tissue to which the primer is applied preferably is first cleaned using conventional methods (e.g., by abrading it with a bur), rinsed (e.g., using water) and dried (e.g., using air). If desired, deep excavations in teeth can be lined with a conventional basing material, (e.g., calcium hydroxide or a glass ionomer cement).

The acid and film former should be allowed to stand on the surface of the hard tissue long enough to provide the desired degree of priming. The standing time will depend upon the particular acid and film former employed, whether a concurrent or sequential application of acid and film former is employed, the type of hard tissue and its intended use, and the time available for carrying out the priming procedure. For priming dentin and enamel, standing times less than about 5 minutes, and preferably about 5 seconds to one minute provide very effective priming, although shorter or longer times can be used if desired.

As mentioned above, the primer preferably is overcoated with an optional layer of additional water-dispersible or water-indispersible film former, and then hardened. Preferably, such additional film former is copolymerizable with the residual film formed by removal of volatile cosolvents from the primer, and contains a polymerization catalyst (preferably a photoinitiator) capable of hardening the residual film and additional film former. If desired, the additional film former can contain conventional fillers, and can also contain adjuvants of the type described above. A particularly preferred additional film former is obtained by combining (1) the dimethacrylate ("CBis-GMA") derived from the reaction between methacrylic acid and the diglycidyl ether of bisphenol A with (2) a hydrophilic monomer such as HEMA, hydroxypropyl methacrylate, or methacrylic acid. Suitable monomers for use in the additional film former include the monomers described above as well as tetrahydrofurfural methacrylate, glyceryl-1,3-dimethacrylate, triethyleneglycol dimethacrylate, ethyl methacrylate, n-hexyl methacrylate, polyethyleneglycol dimethacrylate ("PEGDMA"), and 1,6-hexanediol dimethacrylate. Optionally, the additional film former may contain polymers of the type described above. The additional film former can also contain cosolvents of the type described above.

Polymerization catalysts that can be included in the primer or in the additional film former are autocure or light cure catalysts (i.e., catalysts which are sensitive to actinic radiation such as visible light) such as those mentioned in columns 28 and 29 of U.S. Pat. No. 4,539,382, chromophore-substituted halomethyl-s-triazines such as those shown in U.S. Pat. No. 3,954,475, chromophore-substituted halomethyl-oxadiozoles such as those shown in U.S. Pat. No. 4,212,970, and aryliodonium salts such as those shown in European Patent Application 0 290 133.

As also mentioned above, the primer and optional additional film former preferably are overcoated with a conventional restorative or coating. The hard tissue can then be finished using conventional techniques. For example, on tooth tissue, the primer can be overcoated with a dental adhesive, dental ionomer cement and/or a dental restorative and used, for example, to restore teeth, to install crowns, bridgework or other prosthetic devices, to bond orthodontic brackets to enamel, to seal pits and fissures or to veneer dentin, cementum or enamel. On bone and hoofs, the primer can be used in conjunction with a conventional filled or unfilled bone cement (e.g., a methyl methacrylate-based cement) to repair fractures or to fill defects. On fingernails, the primer can be used in conjunction with a conventional polymerizable fingernail coating to strengthen a fingernail, alter its shape, color or smoothness or fasten an artificial fingernail thereto.

The adhesive compositions of the present invention are particularly well suited for use in the high humidity environment of the mouth. Humidity values encountered in the mouth may fluctuate widely, depending on such factors as respiratory exhalation, fluid perfusion through the dentinal tubules and lack of control of extraneous fluids by the dental practitioner. When any of the above factors are present the hard tissue may be considered to be in a high humidity environment. Surprisingly, high adhesive shear strengths of restoratives on dental hard tissues may be achieved without the need to take extraordinary steps to protect the tissue from exposure to high humidity. For purposes of in-vitro comparisons, bond strength tests should preferably be compared in a room temperature high humidity chamber with a relative humidity greater than about 90%.

Adhesive Strength Test Method Adhesion to dentin or enamel of the primers of the invention was evaluated as follows:

First, teeth (usually five bovine teeth unless otherwise noted) of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 320 silicon carbide paper-backed abrasive and then Grade 600 silicon carbide paper-backed abrasive on the lapidary wheel. The polished teeth were stored in distilled water, and used for testing within 2 hours after polishing. The polished teeth were removed from the water and dried using a stream of compressed air.

Primer compositions were next applied to the prepared tooth surfaces as described in one of the following procedures:

Application Procedure I—A single drop of primer composition (containing varying amounts of acid and film former) was painted onto each of the polished tooth surfaces with a brush and allowed to stand for 30 to 60 seconds. The primer was then blown dry with compressed air and cured using a 20-second irradiation with a "Visilux™ 2" dental curing light (commercially available from 3M).

Application Procedure II—A single drop of primer composition (containing varying amounts of acid and film former) was painted onto each of the polished tooth surfaces with a brush, allowed to stand for 30 to 60 seconds, and then blown dry with compressed air. An overcoat of additional water-dispersible or water-indispersible film former was applied, gently air thinned and cured using a 20-second irradiation with a Visilux 2 dental curing light.

Application Procedure III—An etchant was painted onto each of the polished tooth surfaces with a brush, allowed to stand for 15 seconds, and then blown dry with compressed air. A single drop of primer composition (containing varying amounts of acid and film former) was painted onto each of the polished tooth surfaces with a brush and immediately blown dry with compressed air. A thin layer of overcoat of additional water-dispersible or water-indispersible film former was painted onto each of the tooth surfaces, gently air thinned and cured using a 10-second irradiation with a Visilux 2 dental curing light.

Application Procedure IV—An etchant was painted onto each of the polished tooth surfaces with a brush, allowed to stand for 15 seconds (unless otherwise noted), rinsed with distilled water and then blown dry with compressed air. A single drop of primer composition (containing varying amounts of acid and film former) was painted onto each of the polished tooth surfaces with a brush and immediately blown dry with compressed air. A thin overcoat of additional water-dispersible or water-indispersible film former was painted onto each of the tooth surfaces, gently air thinned and cured using a 10-second irradiation with a Visilux 2 dental curing light.

Application Procedure V—In a high humidity chamber (having a temperature of 25 ° C. and a relative humidity greater than 90% ) an etchant was painted onto each of the polished tooth surfaces with a brush, allowed to stand for 15 seconds (unless otherwise noted), rinsed with distilled water and then blown with compressed air. A single drop of primer composition (containing varying amounts of acid and film former) was painted onto each of the polished tooth surfaces with a brush and immediately blown with compressed air. A thin overcoat of additional water-dispersible or water-indispersible film former was painted onto each of the tooth surfaces, gently air thinned and cured using a 10-second irradiation with a Visilux 2 dental curing light.

Previously prepared molds made from a 2-mm thick "Teflon" sheet with a 4 mm diameter hole through the sheet were clamped to each prepared tooth so that the central axis of the hole in the mold was normal to the tooth surface. The hole in each mold was filled with a visible light-curable dental restorative (typically "P-50™" brand universal shade restorative, available from 3M) and cured using a 20-second irradiation. It is believed that the choice of restorative might affect the bond strength values obtained for a given adhesive system. For example, some adhesive systems of the present invention provide very strong bonds to hard tissue that are believed to fail at the restorative-adhesive interface or within the restorative and not at the adhesive-hard tissue interface. A higher strength restorative may increase the measured bond strength for these adhesive systems. Therefore, comparisons between different adhesive systems should be made, wherever possible, using similar restorative systems. The teeth and molds were allowed to stand for about 5 minutes at room temperature, then stored in distilled water at 37° C. for 24 hours unless otherwise noted. The molds were then carefully removed from the teeth, leaving a molded button of restorative attached to each tooth.

Adhesive strength was evaluated by mounting the acrylic disk in a holder clamped in the jaws of an "Instron" apparatus with the polished tooth surface oriented parallel to the direction of pull. A loop of orthodontic wire (0.44 mm diameter) was placed around the restorative button adjacent to the polished tooth surface. The ends of the orthodontic wire were clamped in,the pulling jaw of the Instron apparatus, thereby placing the bond in shear stress. The bond was stressed until it (or the dentin or button) failed, using a crosshead speed of 2 mm/min.

The following examples are offered to aid in understanding of the present invention and are not to be construed as limiting the scope thereof. Unless otherwise indicated, all parts and percentages are by weight.

EXAMPLE 1

Using the adhesive strength test method outlined above and Application Procedure I, the average shear strength on dentin and enamel of several primer compositions was evaluated. The primers were made from aqueous solutions of various polymers, monomers and optionally maleic acid as listed in Table 1. Set out below in Table I are the run number, ingredients, and average shear strength on enamel or dentin (in MPa.). The sample size (n) for each run in this and the following examples was five unless otherwise noted.

TABLE 1

| Ingredients (parts) | Run # | | | | | | |
|---|---|---|---|---|---|---|---|
| | 1 | 2 | 3 | 4 | 5 | 6[7] | 7[8] |
| VBP[1] | 4.23 | 1.52 | - - | 10.0 | 15.0 | 30.0 | 10.0 |
| VBP-T[2] | - - | - - | 0.76 | - - | - - | - - | - - |
| HEMA | 2.29 | 2.02 | 1.45 | 40.0 | 29.0 | 28.0 | 36.0 |
| PEGDMA | 5.0 | - - | - - | - - | - - | - - | - - |
| Water | 3.43 | 6.43 | 2.80 | 50.0 | 56.0 | 42.0 | 54.0 |
| MOST[3] | 0.075 | - - | - - | - - | - - | - - | - - |
| CPQ[9] | 0.050 | 0.026 | - - | 0.2 | - - | 0.5 | - - |
| Maleic Acid | - - | 0.52 | 0.25 | 4.0 | 5.0 | - - | - - |
| DPICl[10] | - - | - - | - - | - - | - - | 3.2 | - - |
| Adhesion (Mpa.) at 24 hrs. | | | | | | | |
| Enamel | - - | - - | 12.8 | - - | 9.8 | - - | - - |
| Dentin | 12.1[4] | 12.5[5] | 7.7 | 14.6 | 6.4 | 13.8 | 10.6 |
| Adhesion (MPa.) immediate | | | | | | | |
| Dentin | - - | - - | - - | - - | 11.0[6] | - - | - - |

[1]("VBP") = the precipitated dry polymer of EXAMPLE 11 of European Published Pat. Application No. 0 323 120.
[2]("VBP-T") = the reaction product of VBP, "MOSTOL" (2,4-Bis-(trichloromethyl)-6-(2-hydroxyethoxy)styryl-s-triazine), and "TMDI" (Tetramethylene diisocyanate). The preparation of this polymer is described in EXAMPLE 2 below and contains in this example approximately 4% triazine functionality by weight.
[3]("MOST") = 2,4-Bis-(trichloromethyl)-6-methoxystyryl-s-triazine
[4]n = 3
[5]n = 1
[6]n = 2
[7]Run 6 deviated from the standard procedure in that: 1) Silux™ restorative, commercially available from 3M, was used in place of the P-50™ restorative called for in the adhesive strength test method; and 2) the polymer (VBP) had 75% of the customary methacrylate functionality of the precipitated dry polymer of EXAMPLE 11 of European Published Pat. Application No. 0 323 120.
[8]Run 7 deviated from the standard procedure in that Vitrebond™ glass ionomer cement (available from 3M) was used in place of the P-50™ restorative called for in the adhesive strength test method.
[9]("CPQ") = Camphorquinone.
[10]("DPICl") = Diphenyliodonium chloride.

The above data illustrates the adhesion to dentin or enamel obtained when a variety of primers are applied in a single application to the hard tissue. The above runs all contained polymer, monomer and water. Runs 2, 3, 4 and 5 further contained maleic acid.

EXAMPLE 2

Using the adhesive strength test method outlined above and Application Procedure I, the average shear strength on enamel of several primer compositions was evaluated. The primers were formulated from aqueous solutions of various polymers, HEMA, and maleic acid as listed in Table 2. Each primer further contains 0.005 parts CPQ. The polymers used in this example were prepared by reacting VBP, MOSTOL, and TMDI. A solution of 69 parts tetrahydrofuran ("THF") and 6.0 pans MOSTOL was slowly added to a solution of 44.4 parts TFIF, 1.32 parts TMDI and 0.5 pans dibutyltin dilaurate ("DBTDL") and heated at 40° C. for 18 hours with a dry air atmosphere. Four different polymer formulations were prepared by reacting the above solution with VBP polymer. A "3%" triazine functionalized polymer (i.e., approximately 3% of the final polymer weight is represented by the triazine moiety) was prepared by slowly adding 0.75 parts triazine (i.e., not counting the weight attributable to the TMDI component or the solvent) to 25 parts VBP polymer. This reaction was run at 40° C. for 18 hours with DBTDL catalyst and a dry air atmosphere. The resultant polymer was precipitated into ethylacetate and dried in a vacuum oven to remove the solvent. Likewise, by varying the stoichiometry of the triazine and VBP, a 6%, 9%, and 12% triazine functionalized polymer was made. Set out below in Table 2 are the run number, ingredients, and the average shear strength to enamel.

TABLE 2

| Run # | Maleic acid | HEMA | Water | Polymer, VBP-T | % Triazine on polymer | Adhesion to enamel, MPa |
|---|---|---|---|---|---|---|
| 1 | 0.251 | 1.582 | 3.060 | 0.342 | 6 | 12.1 |
| 2 | 0.126 | 2.071 | 2.497 | 0.434 | 9 | 16.2 |
| 3 | 0.250 | 2,552 | 1.918 | 0.523 | 6 | 11.2 |
| 4 | 0.127 | 1.078 | 3.349 | 0.582 | 3 | 13.0 |
| 5 | 0.375 | 1.072 | 3.340 | 0.582 | 3 | 15.6 |
| 6 | 0.252 | 1.470 | 2.791 | 0.760 | 0 | 8.5 |
| 7 | 0.250 | 1.445 | 2.795 | 0.760 | 12 | 11.5 |
| 8 | 0.000 | 1.442 | 2.807 | 0.760 | 6 | 7.4 |
| 9 | 0.251 | 1.446 | 2,792 | 0.761 | 6 | 15.0 |
| 10 | 0.500 | 1.444 | 2.793 | 0.761 | 6 | 13.0 |
| 11 | 0.249 | 0.692 | 3.406 | 0.924 | 6 | 12.0 |
| 12 | 0.249 | 1.203 | 2.292 | 1.524 | 6 | 7.0 |

EXAMPLE 3

Using the adhesive strength test method outlined above and Application Procedure II, the average shear strength on dentin and enamel of several primer compositions was evaluated. The primers were formulated from aqueous solutions of VBP polymer, HEMA and maleic acid as listed in Table 3. The additional film former was comprised of 61.9 parts Bis-GMA, 37.1 pans HEM& 0.25 pans CPQ, 0.25 parts diphenyliodonium hexafluorophosphate ("DPIHFP"), and 0.50 pans ethyl 4-dimethylaminobenzoate ("EDMAB"). Set out below in Table 3 are the run number, ingredients, and the average shear strength on enamel and dentin in MPa.

TABLE 3

| Run # | Maleic acid | HEMA | Water | Polymer, VBP-T | Adhesion to enamel, MPa | Adhesion to dentin, MPa |
|---|---|---|---|---|---|---|
| 1 | 0.501 | 2.487 | 7.105 | 0.003 | 18.5 | 6.1 |
| 2 | 0.507 | 1.029 | 8.451 | 0.032 | 23.5 | 7.9 |
| 3 | 0.803 | 2.328 | 6.796 | 0.073 | 19.4 | 7.1 |
| 4 | 0.527 | 2.405 | 7.006 | 0.077 | 20.1 | 13.6 |
| 5 | 0.202 | 2.484 | 7.229 | 0.080 | 15.8 | 17.8 |
| 6 | 0.501 | 4.604 | 4.751 | 0.144 | 17.8 | 27.9 |
| 7 | 0.324 | 1.301 | 8.133 | 0.236 | 26.6 | 16.4 |
| 8 | 0.500 | 1.500 | 7.500 | 0.500 | 23.7 | 19.7 |
| 9 | 0.329 | 3.290 | 5.805 | 0.588 | 21.3 | 26.8 |
| 10 | 0.502 | 1.244 | 7.005 | 1.243 | 23.8 | 15.1 |

Additional specimens of run 8 were prepared and stored in distilled water at 37° C. At time intervals of seven days, one month, and three months, specimens were removed from the water and tested as described above. The average shear strength on dentin and enamel at each time is shown in Table 4 below.

TABLE 4

| Time in 37° C. water | Adhesion to enamel, MPa | Adhesion to dentin, MPa |
|---|---|---|
| 24 hr. | 23.7 | 19.7 |
| 7 days | 26.5 | 21.2 |
| 1 month | 32.7 | 26.8 |
| 3 months | 23.7 | 20.1 |

The above data (in Tables 3 and 4) illustrates the adhesion to dentin and enamel obtained when a variety of primers are employed through a single application to the hard tissue followed by an overcoat of additional film former. The data of Table 4 illustrates the excellent stability of the bond upon exposure to aqueous environments for a prolonged period.

EXAMPLE 4

Using the adhesive strength test method outlined above and Application Procedure III, the average shear strength on dentin and enamel of a primer composition was evaluated. The etchant was comprised of 8 parts maleic acid and 92 parts water; the primer solution contained 13.3 parts VBP polymer, 39.8 parts HEMA and 46.9 parts water, and the additional film former contained 61.9 parts Bis-GMA, 37.1 parts HEMA 0.25 parts CPQ, 0.25 parts DPIHFP, and 0.50 parts EDMAB. The average shear strength on enamel and dentin was 27.7 MPa. and 16.8 MPa. respectively.

EXAMPLES 5 AND 6

Using the adhesive Strength test method outlined above and Application Procedure IV, the average shear strength on dentin and enamel of two primer compositions was evaluated. The etchant, primer, and additional film former of EXAMPLE 5 are the same as used in EXAMPLE 4. The primer and additional overcoat film former of EXAMPLE 6 were the same as in EXAMPLE 4, however, the etchant of EXAMPLE 6 was a phosphoric acid etching gel containing 35 parts phosphoric acid, 5.5 parts Cabosil (available from Degussa), 0.1 parts methylene blue, and 59.4 parts water. In a like manner to EXAMPLE 3, specimens were tested after storage in water at 37° C. for a period of up to one month.

The results are listed in Table 5 as a function of storage time.

TABLE 5

| Example | Time in 37° C. water | Adhesion to Enamel, MPa. | Adhesion to Dentin, MPa. |
|---|---|---|---|
| 5 | 24 hr. | 27.7 | 30.6 |
| 5 | 7 days | 19.5 | 29.3 |
| 5 | 1 month | 28.4 | 24.1 |
| 6 | 24 hr. | 27.1 | 17.7 |
| 6 | 7 days | 31.4 | 11.2 |
| 6 | 1 month | 38.0 | 17.8 |

The data of Table 5 demonstrates that very acceptable average shear strengths can be achieved using primers that contain either maleic acid or phosphoric acid. The average shear strength to both dentin and enamel was durable and stable over a prolonged period.

EXAMPLE 7

Adhesion to Sclerotic Dentin

The ability to bond to sclerotic dentin is an important feature lacking in currently available adhesive systems. In this example ten human dentin specimens which were characterized as sclerotic were treated using the adhesive strength test method outlined above and Application Procedure IV. The etchant, primer, and the additional film former were the same as used in EXAMPLE 4. The average adhesion value to sclerotic dentin was 17.3 MPa. while a Scotchbond™ 2 control adhesive (available commercially from 3M) provided an average shear strength of less than 3 MPa.

EXAMPLE 8

Effect of Varying Molecular Weight

In this example a series of polyethyleneglycol polymers ("PEG") of varying molecular weights were "end-capped" with itaconic anhydride, with succinic anhydride or with 2-isocyanatoethyl methacrylate ("IEM"). PEG is represented by the following formula:

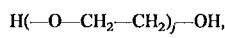

$$H(-O-CH_2-CH_2)_j-OH,$$

wherein the value of j for this series of PEG polymers (and their end-capped derivatives) is listed in Table 6. The preparation of the end-capped polymers involved the stoichiometric reaction of two equivalents of end capping agent to one equivalent of polymer. Itaconic anhydride or succinic anhydride was attached to the PEG molecule by heating the components at 90° C. as a neat solution (i.e., without solvent). The reaction was monitored by nuclear magnetic resonance until disappearance of the starting material at which time the heat was removed. IEM was attached to the PEG molecule by reacting the ingredients in a methylene chloride solution containing 0.4% dibutyltin dilaurate catalyst for 30 minutes at 90° C. The solvent was removed by evaporation using a rotary evaporation apparatus.

Using the adhesive strength test method outlined above and Application Procedure IV, the shear strength on dentin and enamel of various primer compositions was evaluated. The etchant, and additional film former are the same as used in EXAMPLE 4. The primer was comprised of 10 pans of the indicated polymer (as listed in Table 6), 40 pans HEMA, and 50 pans water. Table 6 illustrates the average shear strength on enamel and dentin.

TABLE 6

| Run # | Ave. number of ethylene repeat groups (j) | Final approx. molecular weight (Mw) | End-cap moiety | Adhesion to enamel, MPa. | Adhesion to dentin, MPa. |
|---|---|---|---|---|---|
| 1 | 6.4 | 300 | none | 11.3 | 14.7 |
| 2 | 13.2 | 600 | none | 8.9 | 10.3 |
| 3 | 33.7 | 1,500 | none | 18.6 | 11.8 |
| 4 | 45 | 2,000 | none | 22.8 | 11.0 |
| 5 | 77 | 3,400 | none | 17.6 | 12.2 |
| 6 | 181 | 8,000 | none | 13.1 | 13.1 |
| 7 | 6.4 | 524 | Ita. Anhyd. | 15.1 | 20.5 |
| 8 | 13.2 | 824 | Ita. Anhyd. | 21.2 | 16.0 |
| 9 | 33.7 | 1,724 | Ita. Anhyd. | 17.8 | 20.6 |
| 10 | 45 | 2,224 | Ita. Anhyd. | 18.0 | 18.6 |
| 11 | 77 | 3,624 | Ita. Anhyd. | 18.2 | 11.8 |
| 12 | 181 | 8,224 | Ita. Anhyd. | 20.3 | 9.4 |
| 13 | 6.4 | 500 | Suc. Anhyd. | 16.1 | 23.3 |
| 14 | 13.2 | 800 | Suc. Anhyd. | 12.1 | 17.3 |
| 15 | 33.7 | 1,700 | Suc. Anhyd. | 19.6 | 11.6 |
| 16 | 45 | 2,200 | Suc. Anhyd. | 10.1 | 15.6 |
| 17 | 77 | 3,600 | Suc. Anhyd. | 18.8 | 9.1 |
| 18 | 181 | 8,200 | Suc. Anhyd. | 12.2 | 10.0 |
| 19 | 6.4 | 610 | IEM | 14.6 | 12.7 |
| 20 | 13.2 | 910 | IEM | 16.9 | 10.4 |
| 21 | 33.7 | 1,810 | IEM | 26.3 | 11.4 |
| 22 | 45 | 2,310 | IEM | 11.5 | 9.6 |
| 23 | 77 | 3,710 | IEM | 23.2 | 10.5 |
| 24 | 181 | 8,310 | IEM | 19.4 | 8.6 |

EXAMPLE 9

Adhesion in High Humidity Environment

This example demonstrates the ability of the compositions of the invention to bond to dentin under severe conditions of high humidity (i.e., relative humidity ("RH")>90%). Using the adhesive strength test method outlined above and Application Procedure V, the average shear strength on dentin of various primer compositions was evaluated. The etchant and additional film former are the same as used in EXAMPLE 4. The primer for runs 2–9 contained 10 pans of the indicated polymer (as listed in Table 7), 40 pans HEMA, and 50 pans water. The primer for runs 10–12 contained 13.3 pans polymer, 39.8 parts HEMA, and 46.9 pans water. The primer of run 1, which is included as a control, is composed of 2.5 parts maleic acid, 58.5 pans HEMA, and 39.0 pans water and contains no polymer.

TABLE 7

| Run # | Polymer in the primer | Adhesion to dentin, MPa. | Mol. wt. | End capping group |
|---|---|---|---|---|
| 1 | none[1] | <2.5 | | |
| 2 | Ex. 8, run 4 | 6.8 | 2,000 | none |
| 3 | Ex. 8, run 7 | 8.2 | 524 | Ita. Anhyd. |
| 4 | Ex. 8, run 9 | 5.3 | 1,724 | Ita. Anhyd. |
| 5 | Ex. 8, run 10 | 9.2 | 2,224 | Ita. Anhyd. |
| 6 | Ex. 8, run 11 | 10.9 | 3,624 | Ita. Anhyd. |

TABLE 7-continued

| Run # | Polymer in the primer | Adhesion to dentin, MPa. | Mol. wt. | End capping group |
|---|---|---|---|---|
| 7 | Ex. 8, run 12 | 5.7 | 8,224 | Ita. Anhyd. |
| 8 | Ex. 8, run 16 | 9.9 | 2,200 | Suc. Anhyd. |
| 9 | Ex. 8, run 22 | 11.7 | 2,310 | IEM |
| 10 | VBP3:2[2] | 7.0 | 8,900 | |
| 11 | VBP | 22.4[4] | 20,000 | |
| 12 | AA-IEM[3] | 16.5 | 115,000 | |

[1]Control experiment.
[2]("VBP3:2") = the precipitated dry polymer of EXAMPLE 11 of European Published Pat. Application No. 0 323 120 with a ratio of acrylic acid to itaconic acid of 3:2 instead of 4:1.
[3]("AA-IEM") = the precipitated dry polymer of EXAMPLE 10 of European Published Pat. Application No. 0 323 120.
[4]Average of 15 strength values.

EXAMPLE 10

Effect of Polymer Concentration in the Primer

This example demonstrates the ability of the compositions of the invention to bond to dentin under severe conditions of high humidity (RH >90%). Using the adhesive strength test method outlined above and Application Procedure V, the average shear strength on dentin of various primer compositions was evaluated. The etchant, and additional film former are the same as used in EXAMPLE 4. The composition of the primer is listed in Table 8 and illustrates the effect of varying the amount of polymer from 0% (run #1) to 50% (run 40). As is evident from the adhesion values reported in Table 8 even small amounts of polymer drastically improve performance in a high humidity environment.

TABLE 8

| Run # | HEMA | Water | Polymer, VBP | Adhesion to dentin, MPa. |
|---|---|---|---|---|
| 1 | 40 | 60 | 0 | 0.0 |
| 2 | 40 | 59.95 | 0.05 | 8.1 |
| 3 | 40 | 59 | 1 | 20.8 |
| 4 | 40 | 55 | 5 | 17.4 |
| 5 | 40 | 50 | 10 | 20.0 |
| 6 | 40 | 40 | 20 | 22.1 |
| 7 | 40 | 30 | 30 | 14.6 |
| 8 | 40 | 20 | 40 | 16.3 |
| 9 | 30 | 20 | 50 | 13.6 |

EXAMPLE 11

Using the adhesive strength test method outlined above and Application Procedure IV, the average shear strength on dentin and enamel of a primer composition was evaluated as a function of the standing time and the type of acid. The etchant contained either maleic acid or phosphoric acid in water as listed in Table 9. The primer and the additional film former are the same as used in EXAMPLE 4. Table 9 illustrates the concentration of acid in the aqueous etchant for each run and the resultant average shear strength to enamel and dentin.

TABLE 9

| Run # | Acid | % Acid in etchant | Standing time (sec.) | Adhesion to enamel, MPa. | Adhesion to dentin, MPa. |
|---|---|---|---|---|---|
| 1 | phosphoric | 5.0 | 17.5 | 26.5 | 23.6 |
| 2 | phosphoric | 21.3 | 17.5 | 26.4 | 26.3 |
| 3 | phosphoric | 37.5 | 17.5 | 29.5 | 29.3 |
| 4 | phosphoric | 21.3 | 5.0 | 28.6 | 30.7 |
| 5 | phosphoric | 21.3 | 30.0 | 28.1 | 27.7 |
| 6 | maleic | 2.0 | 17.5 | 23.8 | 16.7 |
| 7 | maleic | 11.0 | 17.5 | 21.9 | 22.0 |
| 8 | maleic | 20.0 | 17.5 | 30.3 | 23.3 |
| 9 | maleic | 11.0 | 30.0 | 26.0 | 23.0 |
| 10 | maleic | 11.0 | 30.0 | 26.0 | 23.0 |

EXAMPLE 12

Comparison of Competitive Dentin Adhesives

This example compares the ability of a composition of this invention and several commercial dentin adhesive systems to bond to dentin under severe conditions of high humidity (RH >90%). Using the adhesive strength test method outlined above and Application Procedure V, the average shear strength on dentin of the composition of Run 2 of EXAMPLE 9 was compared to five commercially available dentin adhesive systems. The commercial products were applied to the prepared dentin as recommended by their respective manufacturers.

TABLE 10(a)

| Run # | Product | Adhesion to dentin, MPa. |
|---|---|---|
| 1 | Run 2 of EXAMPLE 9 | 24.7 |
| 2 | XR-Bond™[1] | 0.6 |
| 3 | Universal Bond ®3[2] | 2.9 |
| 4 | Tenure™[3] | 7.8 |
| 5 | All-Bond™[4] | 5.3 |
| 6 | Scotchbond 2[5] | 2.9 |

[1]XR-Primer™/XR-Bond™ Dentin/Enamel Bonding System available from Kerr Manufacturing Co. USA.
[2]Prisma Universal Bond ®3 Dentin/Enamel Bonding Agent available from L. D. Caulk Division Dentsply Int. Inc. Milford, Del.
[3]Tenure™ Solution Dentin Bonding System available from Den-Mat Corp. Santa Maria, Ca.
[4]All-Bond Universal Dental Adhesive System available from Bisco, Inc. Itasca, Ill.
[5]Scotchbond 2™ Light Cure Dental Adhesive with Scotchprep™ Dentin Primer available from 3M Co. St. Paul, Mn.

The above commercial dentin adhesive systems were also modified by adding 10, 20, or 30% VBP to their respective primer component(s). The modified commercial products were then tested under conditions of high humidity using the adhesive strength test method outlined above and Application Procedure V. Table 10(b) lists the adhesion to dentin obtained and the percentage of VBP added to the primer or primers. The modified commercial products were applied to the prepared dentin as recommended by their respective manufacturers.

TABLE 10(b)

| Run # | Product | % VBP | Adhesion to dentin, MPa. |
|---|---|---|---|
| 1 | XR-Bond™ | 10 | 0.5 |
| 2 | XR-Bond™ | 20 | 7.9 |
| 3 | Universal Bond ®3 | 10 | 0.0 |
| 4 | Universal Bond ®3 | 20 | 1.8 |
| 5 | Universal Bond ®3 | 30 | 0.5 |

TABLE 10(b)-continued

| Run # | Product | % VBP | Adhesion to dentin, MPa. |
|---|---|---|---|
| 6 | Universal Bond ®3[1] | 30 | 5.8 |
| 7 | Tenure™ | 10 | 6.0 |
| 8 | Tenure™ | 20 | 11.7 |
| 9 | All-Bond II™[2] | 10 | 15.7 |
| 10 | All-Bond II™ | 20 | 10.1 |
| 11 | All-Bond II™[3] | 20 | 18.2 |

[1] In this run, the commercial primer was modified by adding 30% VBP and the adhesive of Run 2 Example 9 was substituted for the commercial Universal Bond adhesive.
[2] All-Bond II Dental Adhesive System available from Bisco, Inc. Itasca, Ill.
[3] In this run, the commercial primer was modified by adding 20% VBP and the adhesive of Run 2 Example 9 was substituted for the commercial All Bond II adhesive.

EXAMPLE 13

Using the adhesive strength test method outlined above and Application Procedure I, the average shear strength on dentin and enamel of several primer compositions was evaluated. A "tricure" ionomer composition was applied on top of the primer in place of the P-50™ restorative material. The tricure ionomer was prepared by mixing a powder and a liquid, described below, at a ratio of 2.2:1. The liquid was prepared by mixing the ingredients set out below in Table 11.

TABLE 11

| Ingredients | (parts) |
|---|---|
| VBP | 50 |
| Water | 30 |
| HEMA | 20 |
| DPIHFP | 1.0 |
| CPQ | 0.25 |
| BHT | 0.10 |

The powder contains a glass and two separate granular microcapsules. The glass was prepared by first mixing the ingredients set out below in Table 12. The ingredients were next melted in an arc furnace at about 1350°–1450° C., poured from the furnace in a thin stream and quenched using chill rollers to provide an amorphous single-phase fluoroaluminosilicate glass.

TABLE 12

| Ingredient | Amount |
|---|---|
| $SiO_2$ | 37 |
| $AlF_3$ | 23 |
| SrO | 20 |
| $Al_2O_3$ | 10 |
| $AlPO_4$ | 7 |
| $Na_2AlF_6$ | 6 |
| $P_2O_5$ | 4 |

The glass was ball-milled to provide a pulverized frit with a surface area of 3.0 m2/g measured using-the Brunauer, Emmet and Teller ("BET") method. Four parts "A-174" gamma-methacryloxypropyl trimethoxysilane (Union Carbide Corp.), 0.44 parts glacial acetic acid, 25 parts methanol, and 25 parts water were mixed for 15 minutes at room temperature, yielding a silanol-containing solution. One hundred parts of the above prepared glass-were combined with the silanol treating solution, slurried for 1.5 hours at room temperature, dried overnight at 45° C., and sieved through a 74 μm mesh screen. Granular ascorbic-acid containing spherical microcapsules were formed by mixing 2.38 parts ascorbic acid in 47.62 parts water with 366 parts of a 1% solution of cellulose acetate butyrate-in ethyl acetate. The mixture was maintained at 4° C. by immersing the vessel in a ice-water bath and stirred at 700 rpm. 267 Parts of ice cold n-hexane were added to the solution over a thirty minute period. The granular precipitate was filtered, washed with ice cold n-hexane, dried under vacuum and then deagglomerated in an electric mill. Similarly, potassium persulfate containing spherical microcapsules were prepared by substituting $K_2S_2O_8$ for ascorbic acid.

Tricure powder was prepared by milling together for one hour 100 parts silanol treated glass, 0.55 parts ascorbic acid microcapsules, and 0.1 parts $K_2S_2O_8$ microcapsules.

Primers were made from aqueous solutions of various polymers, HEMA and optionally maleic acid as listed in Table 13. Set out below in Table 13 are the run number, ingredients, and the average shear strength value on enamel or dentin (in MPa.).

TABLE 13

| | Run # | | | | | | |
|---|---|---|---|---|---|---|---|
| Ingredients | 1 | 2 | 3 | 4 | 5 | 6 | 7 |
| VBP | | 13.3 | 13.3 | 10 | | | |
| Polyacrylic acid[1] | | | | | 25 | | |
| HEMA | | 39.8 | 39.8 | 36 | | 40 | |
| Water | 92.0 | 46.9 | 138.9 | 54 | 75 | 60 | 100 |
| Maleic acid | 8.0 | | 8.0 | | | | |
| Adhesion (MPa.) at 24 hrs. | | | | | | | |
| Enamel | 11.8 | 15.8 | 12.0 | 16.9 | 6.2 | | |
| Dentin | | 10.7 | 10.4 | 10.1 | 3.7 | 4.5 | 5.3 |

[1] 20,000 Mw available from B. F. Goodrich

As a control experiment the ionomer cement was applied directly to the hard tissue (i.e., no primer solution was used). The average shear strength on enamel and dentin was only 6.22 and 4.49 MPa. respectively for these specimens. Runs 5–7 are offered as comparative examples.

EXAMPLE 14

Using the adhesive strength test method outlined above and Application Procedure I, the average shear strength on dentin and enamel of several primer compositions was evaluated. The primers contained 10 pans VBP, 54 pans water and 36 parts monomer as listed in Table 14. An ionomer composition, as described in EXAMPLE 13, was applied on top of the primer in place of the P-50 restorative material.

TABLE 14

| Run # | Monomer | Adhesion to dentin, MPa. |
|---|---|---|
| 1 | HEMA | 10.4 |
| 2 | Glycerol dimethacrylate | 10.1 |
| 3 | Glycerol monomethacrylate | 9.4 |
| 4 | Pentaerythritol trimethacrylate | 11.7 |

Five additional samples of run 1 were tested after thermocycling the specimens for over cycles between 8° C. and 57° C. The average shear strength for these specimens was 12.7 MPa. The above data illustrates the adhesion to dentin obtained when various monomers were employed in the primer. The bond strengths were excellent and were stable upon exposure to thermo-cycling stresses.

EXAMPLE 15

A copolymer was prepared by copolymerizing 28.8 parts acrylic acid and 13.0 parts itaconic acid as described in EXAMPLE 3 of European Published Pat. Application No. 0 323 120. Into another flask was charged 22.2 pans isophorone diisocyanate, 22.15 pans THF, 0.05 pans BHT and 0.2 parts DBTDL. The flask was fitted with a reflux condenser, stirrer and addition funnel. A solution of 13.0 pans HEMA dissolved in 22.15 parts THF was added dropwise. When the reaction was complete this solution was added to the copolymer solution previously prepared and allowed to react. The resultant derivitized copolymer was precipitated in ethyl acetate and dried in vacuo. Nuclear magnetic resonance ("NMR") and infrared ("IR") analysis showed the presence of the carboxyl and methacryloyl functional groups. A primer solution was made up by dissolving 1.4 pans of the above polymer in a mixture of 3.5 pans HEMA and 5.1 pans water. Using the adhesive strength test method outlined above and Application Procedure I, the shear strength on dentin and enamel of this primer composition was evaluated. An ionomer composition, as described in EXAMPLE 13, was applied on top of the primer in place of the P-50 restorative material. The average shear strength on enamel and dentin using this primer was 17.9 and 10.4 MPa. respectively, while the average shear strength of the ionomer directly on enamel and dentin (i.e., without the primer) was only 4.7 and 3.8 MPa. respectively.

EXAMPLE 16

Using the adhesive strength test method outlined above and Application Procedure I, the average shear strength on dentin and enamel of several primer compositions was evaluated. An ionomer composition, as described in EXAMPLE 13, was applied on top of the primer in place of the P-50 restorative material. The primers of this example contained 48 pans water, 40 pans HEMA, and 12 pans polymer as listed in Table 15. The polymers of runs 2–4 are essentially the same as VBP except the mole ratio of acrylic acid and itaconic acid was varied. The polymer of run 2 ("VBP7:3"), for example, contained 7 equivalents of acrylic acid to 3 equivalents of itaconic acid. This polymer also contained more IEM functionality than VBP.

TABLE 15

| Run # | Polymer | % Derivitization with IEM | $M_w$ | Adhesion to dentin, Mpa. |
|---|---|---|---|---|
| 1 | VBP | 16 | 18,000 | 9.17 |
| 2 | VBP7:3 | 25 | 11,900 | 11.11 |
| 3 | VBP3:2 | 34 | 9,150 | 9.94 |
| 4 | VBP1:1 | 16 | 6,130 | 10.21 |

Various modifications and alterations of this invention will be apparent to those skilled in the an without departing from the scope and spirit of this invention, and it should be understood that this invention is not limited to the illustrative embodiments set forth herein.

We claim:

1. A method for adhering to or coating hard tissue, comprising the steps of:
   a) applying to said hard tissue adhesively effective amounts of an inorganic or organic acid and a water-dispersible film former, wherein said film former comprises
      i) a polymer comprising an adhesively effective amount of carboxylic acid groups, their salts or their reactive derivative groups and an adhesively effective amount of vinyl groups selected from the group consisting of acrylate groups, methacrylate groups and combinations thereof, said polymer having a weight average molecular weight of at least 1100 and
      ii) a monomer having an adhesively effective amount of vinyl groups selected from the group consisting of acrylate groups, methacrylate groups and combinations thereof;
   wherein said acid, being different from said film former, has a pKa less than or equal to that of phenol; and
   b) hardening said film former.

2. A method according to claim 1, wherein said acid and said film former are concurrently applied as a mixture to said hard tissue.

3. A method according to claim 1, wherein said acid is sequentially applied to said hard tissue and rinsed or thinned from the hard tissue before application of said film former.

4. A method according to claim 1, wherein said monomer is 2-hydroxyethylmethacrylate.

5. A method according to claim 1, wherein said polymer has a weight average molecular weight in the range from 1,100 to 1,000,000.

6. A method according to claim 1, wherein said polymer has a weight average molecular weight in the range from 5,000 to 200,000.

7. A method for adhering to or coating hard tissue, comprising the steps of:
   a) applying to said hard tissue adhesively effective amounts of a water-dispersible film former comprising:
      i) a polymer comprising an adhesively effective amount of carboxylic acid groups, their salts or their reactive derivative groups and an adhesively effective amount of vinyl groups selected from the group consisting of acrylate groups, methacrylate groups and combinations thereof, said polymer having a weight average molecular weight of at least 1100,
      ii) a monomer having an adhesively effective amount of vinyl groups selected from the group consisting of acrylate groups, methacrylate groups and combinations thereof, and
      iii) water; and
   b) hardening said film former by exposing said film former to actinic radiation.

8. A method according to claim 7, wherein said polymer has a weight average molecular weight in the range from 1,100 to 1,000,000.

9. A method according to claim 7, wherein said polymer has a weight average molecular weight in the range from 5,000 to 200,000.

10. A hardenable primer film, said film forming a layer with surface modified hard tissue and prior to being hardened comprising adhesively effective amounts of a water-dispersible film former comprising
   i) a polymer comprising an adhesively effective amount of carboxylic acid groups, their salts or their reactive derivative groups and an adhesively effective amount of vinyl groups selected from the group consisting of acrylate groups, methacrylate groups and combinations thereof, said polymer having a weight average molecular weight of at least 1100,
   ii) a monomer having an adhesively effective amount of vinyl groups selected from the group consisting of acrylate groups, methacrylate groups and combinations thereof.

11. A film according to claim 10, wherein said film further comprises an acid having a pKa less than or equal to that of phenol.

12. A film according to claim 11, wherein said polymer has a weight average molecular weight in the range from 1,100 to 200,000 and said acid has a pKa between about −10 and about +5 and is selected from the group consisting of sulfonic acids, carboxylic acids, dicarboxylic acids, phosphonic acid, phosphoric acid, mineral acids and combinations thereof.

13. A film according to claim 10, wherein said polymer is a polyalkenoic acid further modified by the incorporation of addition polymerizable reactive groups.

14. A film according to claim 10, wherein said film former comprises 2-hydroxyethylmethacrylate.

15. A hardenable primer film according to claim 10, wherein said polymer has a weight average molecular weight in the range from 1,100 to 1,000,000.

16. A hardenable primer film according to claim 10, wherein said polymer has a weight average molecular weight in the range from 5,000 to 200,000 and wherein said film is capable of providing an adhesive shear strength when applied in a high humidity environment of at least 7 MPa.

17. A hardenable primer film according to claim 11, wherein said film is capable of providing an adhesive shear strength when applied in a high humidity environment of at least 5 MPa and said acid, being present in an adhesively effective amount, has a pKa between about −10 and about +5.

18. A hardenable primer film according to claim 11, wherein said film is capable of providing an adhesive shear strength when applied in a high humidity environment of at least 7 MPa and said acid, being present in an adhesively effective amount, has a pKa between about −10 and about +5.

19. A hardenable primer film according to claim 11, wherein said film is capable of providing an adhesive shear strength when applied in a high humidity environment of at least 12 MPa and said acid, being present in an adhesively effective amount, has a pKa between about −10 and about +5.

20. A hardenable primer film according to claim 11, wherein said film is capable of providing an adhesive shear strength of at least 12 MPa and said acid, being present in an adhesively effective amount, has a pKa between about −10 and about +5.

* * * * *